United States Patent [19]

Baetz

[11] 4,110,460
[45] Aug. 29, 1978

[54] 2,3-DIHYDRO-IMIDAZO[2,1-B]-THIAZOLE DERIVATIVES AND APPLICATIONS THEREOF

[75] Inventor: Jacques Louis Edouard Baetz, La Garenne, France

[73] Assignee: Metabio, France

[21] Appl. No.: 774,497

[22] Filed: Mar. 4, 1977

[30] Foreign Application Priority Data

Mar. 10, 1976 [GB] United Kingdom ............... 9517/76

[51] Int. Cl.² .................................. C07D 277/60
[52] U.S. Cl. ............................ 424/270; 260/306.7 T
[58] Field of Search ................. 260/306.7 T; 424/270

[56] References Cited

U.S. PATENT DOCUMENTS 3,274,209  9/1966  Raeymaekers et al. ...... 260/306.7 T
3,455,924  7/1969  Lednicer .................... 260/306.7 T

FOREIGN PATENT DOCUMENTS 1,180,202  2/1970  United Kingdom ............. 260/306.7 T

OTHER PUBLICATIONS

Mazur et al., Chem. Abstracts, 72:12645p (1970).

Primary Examiner—Nicholas S. Rizzo

Attorney, Agent, or Firm—Gordon W. Hueschen

[57] ABSTRACT

This invention relates to 2,3-dihydro-imidazo[2,1-b]-thiazole derivatives of the formula:

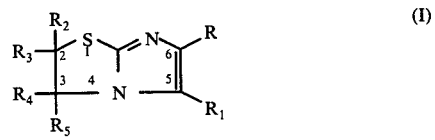

in which
R represents a phenyl or substituted phenyl group,
$R_1$ represents a hydrogen atom or a phenyl substituted with a halogen atom or a $C_{1-4}$ alkoxy group,
$R_2$, $R_3$, $R_4$ and $R_5$, which may be the same or different, represent each a hydrogen atom, a $C_{1-4}$ alkyl group or a phenyl radical,
$R_1$, $R_2$, $R_3$, $R_4$ and $R_5$ not being simultaneously hydrogen when R represents a phenyl group or a phenyl group substituted with a halogen atom or a nitro group, and their pharmaceutically acceptable acid addition salts.

Said compounds have an anti-inflammatory and analgesic activity.

10 Claims, No Drawings

2,3-DIHYDRO-IMIDAZO[2,1-B]-THIAZOLE DERIVATIVES AND APPLICATIONS THEREOF

This invention relates to new 2,3-dihydro-imidazo[2,1-b]-thiazole derivatives having, particularly, an analgesic and anti-inflammatory activity, a process for their preparation and their applications, typically for therapeutic purposes.

A number of 2,3-dihydro-imidazo[2,1-b]-thiazole derivatives are already known. Thus, 2,3-dihydro-imidazo[2,1-b]-thiazoles carrying at 6-position an optionally substituted phenyl group have already been described (Chemical Abstracts, vol. 64, 1966, 2080 h). Some of these compounds have been said as being capable of constituting anthelmintic agents (Chemical Abstracts, vol. 72, 1970, p. 334, 12645 p and Chemical Abstracts, vol. 78, 1973, p. 413, 159620j).

This invention relates to 2,3-dihydro-imidazo[2,1-b]thiazole derivatives having the formula:

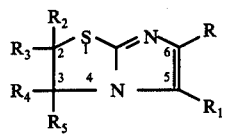

in which R represents a radical of the formula

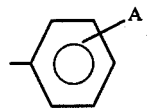

in which A represents a hydrogen atom, a halogen atom, a nitro group, a $C_{1-4}$ alkoxy group, a $C_{1-6}$ alkyl group, a phenyl group, a phenyl group substituted with a halogen atom, a nitro group or a $C_{1-4}$ alkoxy group, or a group of the formula:

$$-CH-COOR_7$$
$$\quad |$$
$$\quad R_6$$

in which
$R_6$ represents hydrogen or a methyl group and $R_7$ represents hydrogen or a $C_{1-6}$ alkyl group,
$R_1$ represents a hydrogen atom or a group of the formula

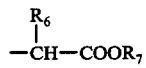

in which
B represents a halogen atom or a $C_{1-4}$ alkoxy group,
$R_2$, $R_3$, $R_4$ and $R_5$, which may be the same or different, represent each a hydrogen atom, a $C_{1-4}$ alkyl group or a phenyl radical,
$R_1$, $R_2$, $R_3$, $R_4$ and $R_5$ not being simultaneously hydrogen when R represents a phenyl group or a phenyl group substituted with a halogen atom or a nitro group,
and their pharmaceutically acceptable acid addition salts.

Among the compounds of the formula (I) are preferred those in which R is a group of the formula

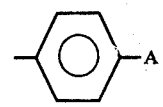

and $R_1$ is a group of the formula

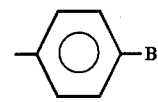

and especially those in which R and $R_1$ are p-methoxyphenyl groups. Particularly preferred compounds include: 2,3-dihydro-5,6-(bis-paramethoxyphenyl)imidazo[2,1-b]thiazole; 2-methyl-2,3-dihydro-5,6-(bis-paramethoxyphenyl)imidazo[2,1-b], thiazole; 3-methyl-2,3-dihydro-5,6-(bis-paramethoxyphenyl)imidazo[2,1-b]thiazole; 2,3-dimethyl-2,3-dihydro-5,6-(bis-paramethoxyphenyl)imidazo[2,1-b]thiazole and their pharmaceutically acceptable acid addition salts.

The compounds of the formula (I) may be prepared by condensation of a 2-aminoΔ2-thiazoline of the formula:

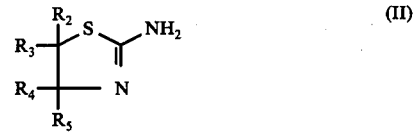

with an alpha-brominated ketone of the formula:

R, $R_1$, $R_2$, $R_3$, $R_4$ and $R_5$ having the meanings given for formula (I).

The reaction may be conducted within a solvent such as chloroform, methylene chloride, acetonitrile. For the preparation of compounds containing no alkoxy group, an alcohol solvent may also be used.

The reaction is advantageously conducted in the presence of an acid binding agent to neutralize the hydrobromic acid released. Said acid binding agent may typically comprise an amine such as triethylamine or an excess of 2-aminoΔ2-thiazoline.

The 2-aminoΔ2-thiazoline may be used as the base or as an addition salt such as the hydrochloride or the hydrobromide, in which case a base is used to shift the 2-aminoΔ2-thiazoline from its salt.

The reaction may generally be effected at a temperature comprised between room temperature and the reflux temperature of the solvent.

The following non limiting examples are given to illustrate the preparations of compounds of the formula (I). In all the Examples, all the melting points were determined with the capillary tube.

EXAMPLE 1

Preparation of
2,3-dihydro-5,6-(bis-paramethoxyphenyl)-imidazo[2,1-b]-thiazole $R = R_1 =$ p.methoxyphenyl; $R_2 = R_3 = R_4 = R_5 = H$ Into a 500 ml Erlenmeyer flask, provided with a magnetic stirring device and a nitrogen bubbling device, are added 59.7 g α-bromodeoxyanisoine (0.178 mole) and 180 ml chloroform. To this solution is added a lukewarm filtered solution containing 36.5 g 2-aminoΔ2-thiazoline (0.356 mole) and 90 ml chloroform.

A temperature rise is found to occur together with the formation of a 2-amino-thiazoline hydrobromide precipitate. The resulting material is stirred at room temperature and under a nitrogen atmosphere during 5.5 hours. The insoluble is then filtered off; after washing with chloroform, the chloroform solution is washed with 6 × 50 ml water; 1 × 50 ml water + a few drops of acetic acid; 2 × 50 ml water; 1 × 50 ml water + sodium bicarbonate to alkaline pH; and finally with 2 × 50 ml water until neutral.

The chloroform phase is dried over anhydrous sodium sulfate, after which it is filtered, rinsed, and evaporated to dryness in a rotary evaporator, to give an oil which is left aside overnight at room temperature.

The resulting material is a partly crystalline oil which is dissolved in 180 ml ethanol. It is then heated to refluxing temperature and refluxed during 1 hour. The solution is concentrated to 50% of its volume in a rotary evaporator, upon which crystallization occurs. The product is placed in a refrigerator during 4 hours, after which it is suction filtered, washed once with ice-cold ethanol and once with ethanol-ether (50:50).

The product is dried overnight, in vacuo, and is then dissolved in refluxing acetonitrile (120 ml). The hot solution is filtered through pre-heated sintered glass. Immediate crystallization occurs in the filtrate. The product is placed in the refrigerator during 4 hours, after which it is suction filtered, washed with ice-cold acetonitrile, dried in vacuo in the presence of potassium hydroxide at room temperature, and then at 80° C, to give 19.4 g of product having a melting point of 157°–158° C.

| Analysis | Calculated | Found |
| --- | --- | --- |
| C | 67.43 | 67.64 |
| H | 5.36 | 5.27 |
| N | 8.28 | 8.40 |
| S | 9.47 | 9.58 |

EXAMPLE 2

Preparation of
2-methyl-2,3-dihydro-5,6-(bis-parachlorophenyl)-imidazo[2,1-b]-thiazole $R = R_1 =$ p.Cl.-phenyl; $R_2 =$ methyl; $R_3 = R_4 = R_5 = H$ Into a 100 ml Erlenmeyer flask, provided with a magnetic stirring device and a nitrogen bubbling device, are added 3.05 g 5-methyl-2-aminoΔ2-thiazoline hydrochloride (0.02 mole), 10 ml chloroform, 5.6 ml triethylamine (0.04 mole), after which a solution containing 6.88 g α-bromo-bis-p-chloro-deoxybenzoine (0.02 mole) and 20 ml chloroform is added thereto.

Complete dissolution occurs. The solution is slightly yellow. It is then stirred during 1 hour, under a nitrogen atmosphere. A white precipitate is found to occur after stirring for 5 minutes.

The product is suction filtered, washed with chloroform and dried in vacuo, to give product A.

The mother liquors and the washing waters are brought to dryness. The residue is taken up into ether. Abundant crystallization occurs. The material is suction filtered, washed with 2 × 10 ml ether, 3 × 10 ml water (removal of the triethylamine salts) and then with 2 × 20 ml ether. The resulting material is dried in vacuo, to give product B.

Products A and B are combined and are suspended in 140 ml ethanol. The suspension is refluxed during 4 hours. Complete dissolution occurs. The solution is concentrated to 50% of its volume at atmospheric pressure. The product is allowed to crystallize out on slow cooling and then left overnight in a refrigerator. It is then suction filtered and washed twice with ethanol, after which it is dried in vacuo, to give 2.350 g of product having a melting point of 199°–200° C (tube).

| Analysis | Calculated | Found |
| --- | --- | --- |
| C | 59.838 | 60.88 |
| H | 3.906 | 3.77 |
| N | 7.754 | 7.61 |
| S | 8.875 | 8.64 |
| Cl | 19.627 | 19.27 |

EXAMPLE 3

Preparation of
2-methyl-2,3-dihydro-5,6-(bis-paramethoxyphenyl)-imidazo[2,1-b]-thiazole $R = R_1 =$ p.methoxyphenyl; $R_2 =$ methyl; $R_3 = R_4 = R_5 = H$ Into a 100 ml Erlenmeyer flask provided with a magnetic stirring device are added 3.05 g 5-methyl-2-aminoΔ2-thiazoline hydrochloride (0.02 mole), 10 ml chloroform, 5.6 ml triethylamine (0.04 mole). A solution containing 6.7 g α-bromo-deoxyanisoine (0.02 mole) and 20 ml chloroform is then added thereto.

The solution is stirred during 5 hours at room temperature. The solution is washed with 4 × 5 ml water. The chloroform phase is dried over sodium sulfate, filtered, rinsed, evaporated to dryness in a rotary evaporator, to give an oil which is dissolved with 40 ml ethanol. The solution is refluxed during 1 hour. It is then concentrated to 50% of its volume in a rotary evaporator and crystallization is promoted by scratching. The product is placed overnight in a refrigerator, after which it is suction filtered, washed with 5 ml ice-cold ethanol and dried in vacuo.

The product is then dissolved in 11 ml refluxing acetonitrile. Crystallization occurs on cooling. The product is placed overnight in a refrigerator, suction filtered, washed with 2× 5 ml ice-cold acetonitrile and dried in vacuo, to give 3.3 g material, m.p. 147°–148° C (tube).

| Analysis | Calculated | Found |
| --- | --- | --- |
| C | 68.155 | 68.67 |
| H | 5.720 | 5.59 |
| N | 7.948 | 7.83 |
| S | 9.097 | 8.99 |

EXAMPLE 4

Preparation of
3-methyl-2,3-dihydro-5,6-(bis-paramethoxyphenyl)-imidazo[2,1-b]-thiazole $R = R_1 = $ p.methoxyphenyl; $R_2 = R_3 = R_5 = H$; $R_4 = $ methyl Into a 100 ml Erlenmeyer flask provided with a magnetic stirring device and with a nitrogen plunger tube are added 10 ml chloroform, 5.6 ml triethylamine (0.04 mole) and 3.05 g 2-amino-4-methylΔ2-thiazoline hydrochloride (0.02 mole). The shifting of the hydrochloride produces a gel. A solution of 6.7 g α-bromo-deoxyanisoine (0.02 mole) and 25 ml chloroform is added thereto, to give a solution which is stirred at room temperature under nitrogen bubbling during 5 hours.

The solution is then washed with 5 × 6 ml water. The organic phase is dried over dry sodium sulfate, filtered, rinsed and brought to dryness in a rotary evaporator, to give an oil which is kept overnight under a nitrogen atmosphere.

This oil is dissolved in 50 ml refluxing ethyl acetate. A slight insoluble is filtered off. The solution is concentrated to about 20 ml. Crystallization occurs. The product is left aside 3 hours at room temperature, after which it is suction filtered, washed with the minimum amount of ethyl acetate and dried overnight in vacuo, to give 1.7 g of a material having a melting point (tube) of 159°–160° C.

| Analysis | Calculated | Found |
|---|---|---|
| C | 68.155 | 68.42 |
| H | 5.720 | 5.72 |
| N | 7.948 | 7.98 |
| S | 9.097 | 9.15 |

EXAMPLE 5

Preparation of
3-methyl-2,3-dihydro-5,6-(bis-parachlorophenyl)-imidazo[2,1-b]-thiazole $R = R_1 = $ p.Cl.phenyl; $R_4 = $ m ethyl; $R_2 = R_3 = R_5 = H$ The procedure described in Example 4 is used. M.P.=218°–219° C.

EXAMPLE 6

Preparation of
2,3-dihydro-6-biphenylyl-imidazo[2,1-b]-thiazole $R = $ biphenylyl; $R_1 = R_2 = R_3 = R_4 = R_5 = H$ The procedure of Example 1 is used. M.P. = 215°–216° C.

EXAMPLE 7

Preparation of
2,3-dimethyl-2,3-dihydro-5,6-bis(p-methoxyphenyl)-imidazo[2,1-b]-thiazole $R = $ p-methoxyphenyl; $R_1 = $ p-methoxyphenyl; $R_2 = R_4 = $ methyl; $R_3 = R_5 = H$ Into a 50 ml Erlenmeyer flask are added 1.8 g 2-amino-4,5-dimethylΔ2-thiazoline hydrochloride (solvatation with 7.6% water; 0.010 mole), 18 ml chloroform and 2.8 ml triethylamine (0.020 mole). When complete dissolution occurs, 3.35 g α-bromodeoxyanosoine (0.010 mole) are added thereto. The resulting mixture is stirred 6 hours at room temperature under a nitrogen atmosphere. The chloroform phase is washed with 5 × 6 ml water; it is then dried and brought to dryness, to give an oil. This oil is then dissolved in 18 ml ethanol and refluxed during 1 hour. The material does not crystallize. The alcohol solution is brought to dryness.

The material is dissolved in methylene chloride and adsorbed on a 50 g Florisil column. Elution is carried out with methylene chloride. The first 75 ml contain no product, after which 10 ml fractions are collected.

The first 12 fractions are brought to dryness, to give an oil which crystallizes. The material is treated with ether and is then left aside at room temperature during 4 hours, after which it is suction filtered, washed and dried in vacuo in the presence of phosphoric anhydride at 50° C, to give 0.750 g of product, m.p. = 120°–121° C.

| Analysis | Calculated | Found |
|---|---|---|
| C | 68.82 | 68.75 |
| H | 6.05 | 5.84 |
| N | 7.64 | 7.72 |
| S | 8.75 | 8.62 |

TABLE I

| Ex. | R | $R_1$ | $R_2$ | $R_3$ | $R_4$ | $R_5$ | Salt | M.p.° C |
|---|---|---|---|---|---|---|---|---|
| 1 | p.methoxyphenyl | p.methoxyphenyl | H | H | H | H | | 157–158 |
| 2 | p.chlorophenyl | p.chlorophenyl | CH$_3$ | H | H | H | | 199–200 |
| 3 | p.methoxyphenyl | p.methoxyphenyl | CH$_3$ | H | H | H | | 147–148 |
| 4 | p.methoxyphenyl | p.methoxyphenyl | H | H | CH$_3$ | H | | 159–160 |
| 5 | p.chlorophenyl | p.chlorophenyl | H | H | CH$_3$ | H | | 218–219 |
| 6 | biphenylyl | H | H | H | H | H | | 215–216 |
| 7 | p.methoxyphenyl | p.methoxyphenyl | CH$_3$ | H | CH$_3$ | H | | 120–121 |
| 8 | –C$_6$H$_4$–CH$_2$COOCH$_3$ | | H | H | H | H | HCl | 172–173 |
| 9 | –C$_6$H$_4$–CH$_2$COOH | | H | H | H | H | | 228–229 |
| 10 | –C$_6$H$_4$–CH$_2$COOH | | H | H | H | H | C$_2$H$_5$ | 210–212 |

TABLE I-continued

| Ex. | R | R₁ | R₂ | R₃ | R₄ | R₅ | Salt | M.p.° C |
|---|---|---|---|---|---|---|---|---|
| 11 | –⟨phenyl⟩–CH₂–COOC₂H₅ | H | H | H | H | CH₃ | HCl | 192–194 |
| 12 | parabromo biphenylyl | H | H | H | H | H | | 293–294 |
| 13 | phenyl | p.methoxyphenyl | H | H | H | H | | 161–162 |
| 14 | ter-butylphenyl | H | H | H | H | H | | 186–188 |
| 15 | p(2-methylpropyl)phenyl | H | H | H | H | H | | 186–187 |
| 16 | p(1-methyl propyl)phenyl | H | H | H | H | H | | 93–95 |
| 17 | p.chlorophenyl | p.chlorophenyl | CH₃ | CH₃ | H | H | | 185–186 |
| 18 | p.methoxyphenyl | p.methoxyphenyl | H | H | H | C₂H₅ | | 165–166 |
| 19 | p.nitrobiphenylyl | H | H | H | H | H | | 310–312 |
| 20 | p.methoxyphenyl | p.methoxyphenyl | H | H | CH₃ | CH₃ | | 236–237 |
| 21 | p.methoxyphenyl | p.methoxyphenyl | C₆H₅ | H | H | H | | 176–177 |
| 22 | p.methoxyphenyl | p.methoxyphenyl | H | H | H | H | HCl | 210–212 |
| 23 | p.methoxybiphenylyl | H | H | H | H | H | | 263–265 |
| 24 | –⟨phenyl⟩–CH(CH₃)–COOH | H | H | H | H | H | | 248–249 |
| 25 | –⟨phenyl⟩–CH(CH₃)–COOC₂H₅ | H | H | H | H | H | HCl | 135–137 |
| 26 | p.chlorophenyl | p.chlorophenyl | H | H | H | H | | 212–213 |

The characteristics of the compounds of Examples 1–7 are tabulated in Table I, together with those of other compounds prepared in an analogous manner.

The results of toxicological and pharmacological investigations are given below. Said results demonstrates the analgesic and anti-inflammatory activities of the compounds of this invention which make them therapeutically valuable.

The anti-inflammatory activity was determined orally, by noting the percent inhibition of carrageenin-induced edema of the rear limb of rats after 1.5 hour.

The anti-inflammatory action of the various compounds is rated, according to its intensity, with 1 + to 4 +'s in the following Table.

The analgesic activity was determined according to the conventional testing methods for said activity: the writhing test. Mice are given a single intraperitoneal injection of 0.2 ml 6°/₁₂₉ acetic acid.

The test compound is administered orally 0.5 hour prior to the acetic acid injection. The number of characteristic writhing movements inducted by pain is recorded during the 15 minutes which follow the acetic acid injection.

The analgesic action of the various derivatives is rated, according to its intensity, with from 1 + to 4 +'s in the following table.

Acute toxicity was determined orally in male mice.

| Compound | LD₅₀ (mg/kg) per os | Anti-inflammatory activity (carrageenin-induced edema) | Analgesic activity (writhing test) |
|---|---|---|---|
| Ex. 1 | >4,200 | ++++ | ++++ |
| Ex. 3 | >2,000 | +++ | +++ |
| Ex. 4 | >2,000 | | +++ |
| Ex. 7 | | +++ | ++++ |
| Ex. 22 | >2,000 | ++++ | ++++ |

In order to demonstrate further the pharmacological activity and the good tolerance of one of the preferred compounds, the 2,3-dihydro-5,6-(bis-paramethoxyphenyl) compound, the specific results obtained with said compound are given below for illustrative purposes.

A. Anti-inflammatory Activity

1. Carrageenin-induced edema in rat

The results of the Table below are expressed in terms of percent inhibition of inflammation of the treated groups, with respect to the reference group, and with respect to phenylbutazone used as reference material:

| | AD₃₀ mg/kg | AD₄₀ mg/kg |
|---|---|---|
| Example 1 | 5.219 | 7.780 |
| Phenylbutazone | 16.112 | 27.446 |

The compound of Example 1 is active from a dosage of 3.38 mg/kg.

2. Cotton-induced granuloma in rat

The test is conducted according to the technique of G.E. ARTH (J. Am. Chem. Soc., 80, 3161, 1958)

The male rats are distributed in randomized groups, slightly anesthetized and depilated in the dorsal area. An incision of about 1 cm is effected along the spine, and 2 pellets of carded cotton weighing each 20 mg are placed under the skin on both sides of the neck.

The treatments are administered orally during 7 days, as suspensions in BT medium. The reference group is administered BT medium alone, under the same experimental conditions. 24 hours after the last ingestion, the pellets are excised and weighed.

The compound of Example 1 inhibits the development of a granuloma. In this test, this compound is twice as active as phenylbutazone.

3. Ultra-violet induced erythema in guinea-pigs

Erythema is induced in depilated guinea-pigs placed at a distance of 25 cm from a 300 watt mercury vapor lamp.

The back of the guinea-pigs is covered with a coat of flexible rubber in which 3 circular perforations 8 mm in diameter are effected. Blind evaluation of the erythema is carried out, 2 hrs and 5 hrs after irradiation.

The treatment is administered by the intragastric route, under a volume of 5 ml/kg.

The protective activity of the compound of Example 1 is proportional to the dosage administered; it is highly marked as early as the first 3 hours, and is still maintained 6 hours after administration.

4. Freund-adjuvant induced arthritis in rats

Injection of *Mycobacterium butyricum* is carried out at the level of the hind limb of rats, and produces as early as the 10th day an arthritis which develops rapidly.

The inhibiting activity of the compound of Example 1 on the development of adjuvant-induced polyarthritis in rats is apparent from a dosage of 5 mg/kg. The criteria used are: the volume of the limb, the X-ray examination of the articulations of the limbs exhibiting inflammation, the weight curve of the animals.

B. Antipyretic Activity

Hyperthermia is induced in rats by subcutaneous injection of barm, at a dosage of 4 g/kg.

The treatments are administered by the intragastric route, 17 hours after yeast injection.

The change in rectal temperature of the rats is compared, as a function of time, in the absolute reference animals, the "barm" reference animals and the treated animals.

The compound of Example 1 is active from a dosage of 3.38 mg/kg.

C. Analgesic Activity

As previously reported, in the acetic acid writhing test in mice the compound of Example 1 has a highly marked analgesic activity on visceral pain in mice.

D. Tolerance in Rats

The chronic toxicity tests conducted in rats at dosages of 40 mg/kg/day failed to provide evidence of any major side-effects on administration of the compound of Example 1.

The low ulcerogenic activity found in fasting rats is equivalent to that of the reference materials.

The compounds of the formula (I) and their pharmaceutically acceptable acid addition salts are therapeutically useful as anti-inflammatory and analgesic agents.

Thus, the present invention includes also within its scope therapeutic compositions comprising, as active ingredient, a compound of the formula (I) or a pharmaceutically acceptable acid addition salt thereof, together with a pharmaceutically acceptable excipient.

Said therapeutic compositions according to the invention may be administered typically by the oral, rectal or topical routes.

The compositions may be formulated as tablets, capsules or in any other orally suitable form, and also as suppositories or ointments. The compositions, in unit dosage form, may contain 10–250 mg active ingredient.

Administration in man may be effected at dosages of 100–1000 mg/day. Such dosages are perfectly well tolerated and the anti-inflammatory activity was found to be satisfactory.

Having now desired my invention what I claim as new and desire to secure by Letters Patent is:

1. A compound selected from the group consisting of compounds of the formula:

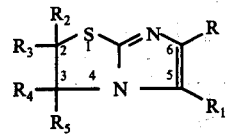 (I)

in which:

R represents a radical having the formula

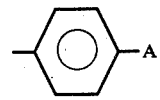

in which A is selected from a hydrogen atom; a chlorine atom; a bromine atom; a nitro group; a $C_{1-4}$ alkoxy group; a $C_{1-6}$ alkyl group; a phenyl group; a phenyl group substituted with a substituent selected from chlorine, bromine, nitro and $C_{1-4}$ alkoxy; and a group of the formula:

$$\underset{|}{R_6}$$
$$-CH-COOR_7$$

in which $R_6$ is selected from hydrogen and methyl, and $R_7$ is selected from hydrogen and $C_{1-6}$ alkyl;

$R_1$ is a group of the formula:

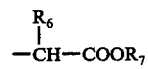

in which B is selected from chlorine, bromine and $C_{1-4}$ alkoxy, $R_2$ is selected from hydrogen, methyl and phenyl,
$R_3$ is selected from hydrogen and methyl,
$R_4$ is selected from hydrogen and methyl,
$R_5$ is selected from hydrogen, methyl and ethyl,
and a pharmaceutically acceptable addition salt thereof.

2. Compounds as claimed in claim 1, wherein R and $R_1$ are p-methoxyphenyl groups.

3. 2,3-Dihydro-5,6-(bis-p-methoxyphenyl)-imidazo[2,1-b]-thiazole and its phramaceutically acceptable acid addition salts.

4. 2-Methyl-2,3-dihydro-5,6-(bis-p-methoxyphenyl)-imidazo[2,1-b]-thiazole and its pharmaceutically acceptable acid addition salts.

5. 3-Methyl-2,3-dihydro-5,6-(bis-p-methoxyphenyl)-imidazo[2,1-b]-thiazole and its pharmaceutically acceptable acid addition salts.

6. 2,3-Dimethyl-2,3-dihydro-5,6-(bis-p-methoxyphenyl)-imidazo[2,1-b]-thiazole and its pharmaceutically acceptable acid addition salts.

7. A therapeutic composition having anti-inflammating and analgesic activities, containing an anti-inflammatory and analgesic effective amount of a compound selected from the group consisting of compounds of the formula:

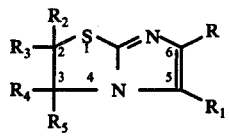 (I)

in which:

R represents a radical having the formula

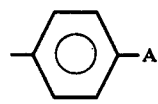

in which A is selected from a hydrogen atom; a chlorine atom; a bromine atom; a nitro group; a $C_{1-4}$ alkoxy group; a phenyl group; a phenyl group substituted with a substituent selected from chlorine, bromine, a nitro and $C_{1-4}$ alkoxy; and a group of the formula:

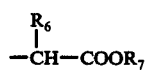

in which $R_6$ is selected from hydrogen and methyl, and $R_7$ is selected from hydrogen and $C_{1-6}$ alkyl; $R_1$ is a group of the formula:

in which B is selected from chlorine, bromine, and $C_{1-4}$ alkoxy, $R_2$ is selected from hydrogen, methyl and phenyl,
$R_3$ is selected from hydrogen and methyl,
$R_4$ is selected from hydrogen and methyl,
$R_5$ is selected from hydrogen, methyl and ethyl, and a pharmaceutically acceptable addition salt thereof, together with a pharmaceutically acceptable excipient.

8. A therapeutic composition as claimed in claim 7 in unit dosage form, each unit dose containing 10–250 mg of active ingredient.

9. A compound as claimed in claim 1, in which A is selected from hydrogen, chlorine and methoxy, and B is selected from chlorine and methoxy.

10. A therapeutic composition as claimed in claim 7, in which A is selected from hydrogen, chlorine and methoxy, and B is selected from chlorine and methoxy.

* * * * *

UNITED STATES PATENT AND TRADEMARK OFFICE
CERTIFICATE OF CORRECTION

PATENT NO. : 4,110,460
DATED : August 29, 1978
INVENTOR(S) : Baetz

It is certified that error appears in the above-identified patent and that said Letters Patent are hereby corrected as shown below:

Title Page, [73] Assignee; "Metobio" should read --Metabio-Joullie--
   Paper No. 10, dated August 2, 1978, Re: decision on the petition filed July 24, 1978, regarding request to correct assignment data of Form PTOL 76-13(b).
Col. 2, lines 20; "(bis-paramethoxyphenyl-"        should read
            21; ")"                        --(bis-paramethoxyphenyl)--
   The end parenthesis should be on the same line as the word it encloses.
Col. 2, line 66; "preparations" should read --preparation--
Col. 5, line 42; "m ethyl;" should read --methyl;--
Col. 7, line 33 & 34; "demonstrates" should read --demonstrate--
Col. 7, line 46; "6°/$_{129}$" should read --6°/$_{00}$--
Col. 7, line 49; "inducted" should read --induced--
Col. 9, line 65; "desired" should read --described--
Col. 10, line 51; "phramaceutically" should read --pharmaceutically--

Signed and Sealed this

Thirteenth Day of March 1979

[SEAL]

Attest:

RUTH C. MASON
Attesting Officer

DONALD W. BANNER
Commissioner of Patents and Trademarks